(12) United States Patent
Pianca et al.

(10) Patent No.: US 9,675,795 B2
(45) Date of Patent: Jun. 13, 2017

(54) SYSTEMS AND METHODS FOR RADIAL STEERING OF ELECTRODE ARRAYS

(75) Inventors: Anne Margaret Pianca, Santa Monica, CA (US); Michael Adam Moffitt, Valencia, CA (US)

(73) Assignee: Boston Scientific Neuromodulation Corporation, Valencia, CA (US)

(*) Notice: Subject to any disclaimer, the term of this patent is extended or adjusted under 35 U.S.C. 154(b) by 1252 days.

(21) Appl. No.: 13/176,595

(22) Filed: Jul. 5, 2011

(65) Prior Publication Data
US 2012/0016378 A1   Jan. 19, 2012

Related U.S. Application Data

(60) Provisional application No. 61/364,960, filed on Jul. 16, 2010.

(51) Int. Cl.
*A61N 1/05* (2006.01)
*A61N 1/36* (2006.01)

(52) U.S. Cl.
CPC ....... *A61N 1/0534* (2013.01); *A61N 1/36182* (2013.01)

(58) Field of Classification Search
CPC .............. A61N 1/36182; A61N 1/0534; A61N 1/00529; A61N 2001/086; A61B 2090/3966; A61B 2090/3937
USPC .................... 606/129; 607/115–117; 29/847; 128/898–899; 600/373, 374
See application file for complete search history.

(56) References Cited

U.S. PATENT DOCUMENTS

| | | | |
|---|---|---|---|
| 4,447,239 A | 5/1984 | Kruetten | |
| 4,541,440 A | 9/1985 | Parsonnet | |
| 4,602,624 A | 7/1986 | Naples et al. | |
| 4,630,611 A | 12/1986 | King | |
| 4,744,370 A | 5/1988 | Harris | |
| 5,000,194 A | 3/1991 | van den Honert et al. | |
| 5,135,001 A | 8/1992 | Sinofsky et al. | |
| 5,374,285 A | 12/1994 | Vaiani et al. | |
| 5,458,629 A | 10/1995 | Baudino et al. | |
| 5,522,874 A | 6/1996 | Gates | |
| 5,711,316 A | 1/1998 | Elsberry et al. | |
| 5,713,922 A | 2/1998 | King | |
| 5,800,350 A | 9/1998 | Coppleson et al. | |
| 5,824,030 A * | 10/1998 | Yang et al. | 607/122 |

(Continued)

FOREIGN PATENT DOCUMENTS

EP    0580928 A1    2/1994
EP    0650694 B1    7/1998

(Continued)

OTHER PUBLICATIONS

U.S. Appl. No. 13/275,112, filed Oct. 17, 2011.

(Continued)

*Primary Examiner* — Katherine Rodjom
(74) *Attorney, Agent, or Firm* — Lowe Graham Jones PLLC; Bruce E. Black (57) ABSTRACT

A device for brain stimulation includes a lead having a longitudinal surface, a proximal end and a distal end. A plurality of electrodes are disposed along the longitudinal surface of the lead near the distal end of the lead. At least one marker is disposed on the longitudinal surface of the lead. The at least one marker is configured and arranged to identify a relative position of the plurality of electrodes.

20 Claims, 10 Drawing Sheets

(56) References Cited

U.S. PATENT DOCUMENTS

| | | |
|---|---|---|
| 5,843,148 A | 12/1998 | Gijsbers et al. |
| 5,938,688 A | 8/1999 | Schiff |
| 5,987,361 A | 11/1999 | Mortimer |
| 6,018,684 A | 1/2000 | Bartig et al. |
| 6,134,478 A | 10/2000 | Spehr |
| 6,161,047 A | 12/2000 | King et al. |
| 6,167,311 A | 12/2000 | Rezai |
| 6,322,559 B1 | 11/2001 | Daulton et al. |
| 6,510,347 B2 | 1/2003 | Borkan |
| 6,556,873 B1 | 4/2003 | Smits |
| 6,564,078 B1 | 5/2003 | Marino et al. |
| 6,678,564 B2 | 1/2004 | Ketterl et al. |
| 6,757,970 B1 | 7/2004 | Kuzma et al. |
| 7,027,852 B2 | 4/2006 | Helland |
| 7,047,084 B2 | 5/2006 | Erickson et al. |
| 7,292,890 B2 | 11/2007 | Whitehurst et al. |
| 7,489,971 B1 | 2/2009 | Franz |
| 7,668,601 B2 | 2/2010 | Hegland et al. |
| 7,761,985 B2 | 7/2010 | Hegland et al. |
| 7,840,188 B2 | 11/2010 | Kurokawa |
| 7,848,802 B2 | 12/2010 | Goetz et al. |
| 7,856,707 B2 | 12/2010 | Cole |
| 7,860,570 B2 | 12/2010 | Whitehurst et al. |
| 7,974,705 B2 | 7/2011 | Zdeblick et al. |
| 7,979,140 B2 | 7/2011 | Schulman |
| 8,000,808 B2 | 8/2011 | Hegland et al. |
| 8,019,440 B2 | 9/2011 | Kokones et al. |
| 8,036,755 B2 | 10/2011 | Franz |
| 8,041,309 B2 | 10/2011 | Kurokawa |
| 8,099,177 B2 | 1/2012 | Dahlberg |
| 8,225,504 B2 | 7/2012 | Dye et al. |
| 8,295,944 B2 | 10/2012 | Howard et al. |
| 8,583,237 B2 | 11/2013 | Bedenbaugh |
| 2002/0156513 A1 | 10/2002 | Borkan |
| 2002/0183817 A1 | 12/2002 | Van Venrooij et al. |
| 2003/0009207 A1* | 1/2003 | Paspa et al. ............... 607/116 |
| 2005/0015130 A1* | 1/2005 | Gill ............................. 607/116 |
| 2005/0038489 A1 | 2/2005 | Grill |
| 2005/0171587 A1* | 8/2005 | Daglow et al. ........... 607/116 |
| 2006/0025841 A1 | 2/2006 | McIntyre |
| 2006/0149335 A1 | 7/2006 | Meadows |
| 2006/0247697 A1 | 11/2006 | Sharma et al. |
| 2007/0203546 A1 | 8/2007 | Stone et al. |
| 2008/0103580 A1 | 5/2008 | Gerber |
| 2008/0114230 A1 | 5/2008 | Addis |
| 2008/0215125 A1 | 9/2008 | Farah et al. |
| 2009/0204192 A1* | 8/2009 | Carlton et al. ............. 607/116 |
| 2009/0204193 A1* | 8/2009 | Kokones et al. ........... 607/116 |
| 2009/0248111 A1* | 10/2009 | Pianca et al. .............. 607/46 |
| 2010/0036468 A1 | 2/2010 | Decre et al. |
| 2010/0076535 A1 | 3/2010 | Pianca et al. |
| 2010/0082076 A1 | 4/2010 | Lee et al. |
| 2010/0094387 A1 | 4/2010 | Pianca et al. |
| 2010/0179626 A1* | 7/2010 | Pilarski et al. ........... 607/116 |
| 2010/0268298 A1 | 10/2010 | Moffitt et al. |
| 2010/0269338 A1 | 10/2010 | Dye |
| 2010/0269339 A1 | 10/2010 | Dye et al. |
| 2010/0287770 A1 | 11/2010 | Dadd et al. |
| 2011/0005069 A1 | 1/2011 | Pianca |
| 2011/0047795 A1 | 3/2011 | Turner et al. |
| 2011/0056076 A1 | 3/2011 | Hegland et al. |
| 2011/0077699 A1 | 3/2011 | Swanson et al. |
| 2011/0078900 A1 | 4/2011 | Pianca et al. |
| 2011/0130803 A1 | 6/2011 | McDonald |
| 2011/0130816 A1 | 6/2011 | Howard et al. |
| 2011/0130817 A1 | 6/2011 | Chen |
| 2011/0130818 A1 | 6/2011 | Chen |
| 2011/0131808 A1 | 6/2011 | Gill |
| 2011/0238129 A1 | 9/2011 | Moffitt et al. |
| 2011/0245903 A1 | 10/2011 | Schulte et al. |
| 2011/0313500 A1 | 12/2011 | Barker et al. |
| 2012/0046710 A1 | 2/2012 | DiGiore et al. |
| 2012/0071949 A1 | 3/2012 | Pianca et al. |
| 2013/0197424 A1 | 8/2013 | Bedenbaugh |
| 2014/0039587 A1 | 2/2014 | Romero |

FOREIGN PATENT DOCUMENTS

| | | |
|---|---|---|
| EP | 0832667 B1 | 2/2004 |
| EP | 1181947 B1 | 1/2006 |
| EP | 2092952 A1 | 8/2009 |
| WO | 9618339 A1 | 6/1996 |
| WO | 9732628 A1 | 9/1997 |
| WO | 9955411 A3 | 2/2000 |
| WO | 0038574 A1 | 7/2000 |
| WO | 0158520 A1 | 8/2001 |
| WO | 02068042 A1 | 9/2002 |
| WO | 2004045707 A1 | 6/2004 |
| WO | 2008018067 A2 | 2/2008 |
| WO | 2008053789 A1 | 5/2008 |
| WO | 2009025816 A1 | 2/2009 |
| WO | 2009102536 A1 | 8/2009 |
| WO | 2013162775 A2 | 10/2013 |
| WO | 2014018092 A1 | 1/2014 |

OTHER PUBLICATIONS

U.S. Appl. No. 13/363,059, filed Jan. 31, 2012.
U.S. Appl. No. 13/368,982, filed Feb. 8, 2012.
U.S. Appl. No. 13/369,013, filed Feb. 8, 2012.
U.S. Appl. No. 13/368,733, filed Feb. 8, 2012.
International Search Report and Written Opinion, PCT/US2011/042981, mailed Jan. 31, 2012.
U.S. Appl. No. 13/787,171, filed Mar. 6, 2013.
U.S. Appl. No. 13/750,725, filed Jan. 25, 2013.
U.S. Appl. No. 13/899,316, filed May 21, 2013.
U.S. Appl. No. 13/906,776, filed May 31, 2013.
U.S. Appl. No. 14/286,940, filed May 23, 2014.
U.S. Appl. No. 14/286,889, filed May 23, 2014.
U.S. Appl. No. 14/286,934, filed May 23, 2014.
U.S. Appl. No. 14/325,249, filed Jul. 7, 2014.
U.S. Appl. No. 14/332,212, filed Jul. 15, 2014.
U.S. Appl. No. 14/452,461, filed Aug. 5, 2014.
U.S. Appl. No. 14/286,829, filed May 23, 2014.
U.S. Appl. No. 14/469,214, filed Aug. 26, 2014.
U.S. Appl. No. 14/286,797, filed May 23, 2014.

* cited by examiner

SYSTEMS AND METHODS FOR RADIAL STEERING OF ELECTRODE ARRAYS

CROSS-REFERENCE TO RELATED APPLICATIONS

This application claims the benefit under 35 U.S.C. §119 (e) of U.S. Provisional Patent Application Ser. No. 61/364,960 filed on Jul. 16, 2010, which is incorporated herein by reference.

FIELD

The invention is directed to devices and methods for brain stimulation including deep brain stimulation. In addition, the invention is directed to devices and method for brain stimulation using a lead having at least one marker to identify the position of the plurality of electrodes.

BACKGROUND

Deep brain stimulation can be useful for treating a variety of conditions including, for example, Parkinson's disease, dystonia, essential tremor, chronic pain, Huntington's Disease, levodopa-induced dyskinesias and rigidity, bradykinesia, epilepsy and seizures, eating disorders, and mood disorders. Typically, a lead with a stimulating electrode at or near a tip of the lead provides the stimulation to target neurons in the brain. Magnetic resonance imaging (MRI) or computerized tomography (CT) scans can provide a starting point for determining where the stimulating electrode should be positioned to provide the desired stimulus to the target neurons.

Upon insertion, current is introduced along the length of the lead to stimulate target neurons in the brain. This stimulation is provided by electrodes, typically in the form of rings, disposed on the lead. The current projects from each electrode similarly and in all directions at any given length along the axis of the lead. Because of the shape of the electrodes, radial selectivity of the current is minimal. This results in the unwanted stimulation of neighboring neural tissue, undesired side effects and an increased duration of time for the proper therapeutic effect to be obtained.

In the field of deep brain stimulation, radially segmented electrode arrays (RSEA) have been developed to provide superior radial selectivity of current. Radially segmented electrode arrays are useful for deep brain stimulation because the target structures in the deep brain are often not symmetric about the axis of the distal electrode array. In some cases, a target may be located on one side of a plane running through the axis of the lead. In other cases, a target may be located at a plane that is offset at some angle from the axis of the lead. Thus, it is desirable to be able to radially adjust the location of the lead such that the appropriate level of electrodes is in optimum radial alignment with the target tissue.

BRIEF SUMMARY

One embodiment is a device for brain stimulation includes a lead having a longitudinal surface, a proximal end and a distal end. A plurality of electrodes are disposed along the longitudinal surface of the lead near the distal end of the lead. At least two marking stripes are disposed on the longitudinal surface of the lead. The marking stripes are configured and arranged to identify a relative position of the plurality of electrodes.

Another embodiment is a device for brain stimulation includes a lead having a longitudinal surface, a proximal end and a distal end. A plurality of electrodes are disposed along the longitudinal surface of the lead near the distal end of the lead. At least one colored cable is disposed longitudinally within the lead. The at least one colored cable is configured and arranged to identify a relative position of the plurality of electrodes. a colored cable.

Yet another embodiment is a device for brain stimulation includes a lead having a longitudinal surface, a proximal end and a distal end. The lead defines a lumen extending longitudinally along the lead with the lumen having a non-circular cross-section. A plurality of electrodes are disposed along the longitudinal surface of the lead near the distal end of the lead. A longitudinally keyed feature is disposed along the proximal end of the lead. The device also includes an aligning member insertable into the lumen of the lead. The aligning member includes a keyed feature that engages the keyed feature along the proximal end of the lead. The aligning member has a non-circular cross-section corresponding to the non-circular cross-section of the lumen.

Another embodiment is a method for brain stimulation. The method includes inserting a device into a cranium of a patient. The device includes a lead having a longitudinal surface, a proximal end and a distal end; a plurality of electrodes disposed along the longitudinal surface of the lead near the distal end of the lead; and at least two marking stripes disposed on the longitudinal surface of the lead. The marking stripes are configured and arranged to identify a relative position of the plurality of electrodes. The method further includes aligning the lead to a selected position using the at least two marking stripes.

Another embodiment is a method for brain stimulation. The method includes inserting a device into a cranium of a patient. The device includes a lead having a longitudinal surface, a proximal end and a distal end; a plurality of electrodes disposed along the longitudinal surface of the lead near the distal end of the lead; and at least one colored cable disposed longitudinally within the lead. The at least one colored cable is configured and arranged to identify a relative position of the plurality of electrodes. a colored cable. The method further includes aligning the lead to a selected position using the at least one colored cable.

Another embodiment is a method for brain stimulation. The method includes inserting a device into a cranium of a patient. The device includes a lead having a longitudinal surface, a proximal end and a distal end; a plurality of electrodes disposed along the longitudinal surface of the lead near the distal end of the lead; a longitudinally keyed feature disposed along the proximal end of the lead; and an aligning member insertable into the lumen of the lead. The aligning member includes a keyed feature that engages the keyed feature along the proximal end of the lead. The lead defines a lumen having a non-circular cross-section and the aligning member has a non-circular cross-section corresponding to the non-circular cross-section of the lumen. The method further includes aligning the lead to a selected position using the aligning member.

BRIEF DESCRIPTION OF THE DRAWINGS

Non-limiting and non-exhaustive embodiments of the present invention are described with reference to the following drawings. In the drawings, like reference numerals refer to like parts throughout the various figures unless otherwise specified.

For a better understanding of the present invention, reference will be made to the following Detailed Description, which is to be read in association with the accompanying drawings, wherein.

DETAILED DESCRIPTION

The present invention is directed to the area of devices and methods for brain stimulation including deep brain stimulation. In addition, the invention is directed to devices and method for brain stimulation using a lead having a plurality of segmented electrodes.

A lead for deep brain stimulation may include stimulation electrodes, recording electrodes, or a combination of both. A practitioner may determine the position of the target neurons using the recording electrode(s) and then position the stimulation electrode(s) accordingly without removal of a recording lead and insertion of a stimulation lead. In some embodiments, the same electrodes can be used for both recording and stimulation. In some embodiments, separate leads can be used; one with recording electrodes which identify target neurons, and a second lead with stimulation electrodes that replaces the first after target neuron identification. A lead may include recording electrodes spaced around the circumference of the lead to more precisely determine the position of the target neurons. In at least some embodiments, the lead is rotatable so that the stimulation electrodes can be aligned with the target neurons after the neurons have been located using the recording electrodes.

Deep brain stimulation devices and leads are described in the art. See, for instance, U.S. Patent Publication 2006/0149335 A1 ("Devices and Methods For Brain Stimulation"), and co-pending patent application U.S. Ser. No. 12/237,888 ("Leads With Non-Circular-Shaped Distal Ends For Brain Stimulation Systems and Methods of Making and Using"). Each of these references is incorporated herein by reference in its respective entirety.

Figure 10:
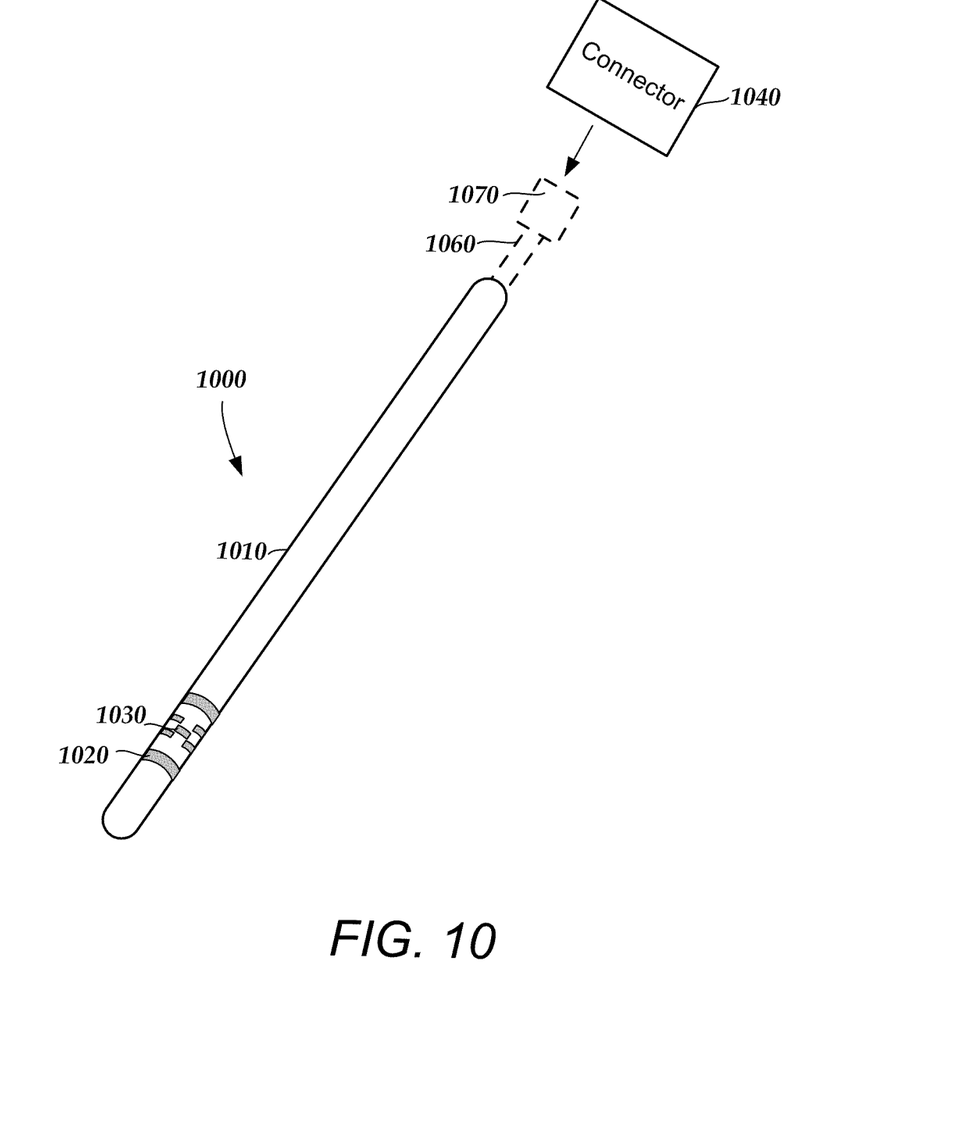
FIG. 10 is a schematic side view of one embodiment of a device for brain stimulation, according to the invention.

FIG. 10 illustrates one embodiment of a device 1000 for brain stimulation. The device includes a lead 1010, ring electrodes 1020, segmented electrodes 1030, a connector 1040 for connection of the electrodes to a control unit, and a stylet 1060 for assisting in insertion and positioning of the lead in the patient's brain. The stylet 1060 can be made of a rigid material. Examples of suitable materials include tungsten, stainless steel, or plastic. The stylet 1060 may have a handle 1070 to assist insertion into the lead, as well as rotation of the stylet and lead. The connector 1040 fits over the proximal end of the lead 1010, preferably after removal of the stylet 1060.

In one example of operation, access to the desired position in the brain can be accomplished by drilling a hole in the patient's skull or cranium with a cranial drill (commonly referred to as a burr), and coagulating and incising the dura mater, or brain covering. The lead 1010 can be inserted into the cranium and brain tissue with the assistance of the stylet 1060. The lead can be guided to the target location within the brain using, for example, a stereotactic frame and a microdrive motor system. In some embodiments, the microdrive motor system can be fully or partially automatic. The microdrive motor system may be configured to perform one or more the following actions (alone or in combination): rotate the lead, insert the lead, or retract the lead. In some embodiments, measurement devices coupled to the muscles or other tissues stimulated by the target neurons or a unit responsive to the patient or clinician can be coupled to the control unit or microdrive motor system. The measurement device, user, or clinician can indicate a response by the target muscles or other tissues to the stimulation or recording electrode(s) to further identify the target neurons and facilitate positioning of the stimulation electrode(s). For example, if the target neurons are directed to a muscle experiencing tremors, a measurement device can be used to observe the muscle and indicate changes in tremor frequency or amplitude in response to stimulation of neurons. Alternatively, the patient or clinician may observe the muscle and provide feedback.

It will be understood that the lead 1010 for deep brain stimulation can include stimulation electrodes, recording electrodes, or both. In at least some embodiments, the lead is rotatable so that the stimulation electrodes can be aligned with the target neurons after the neurons have been located using the recording electrodes.

Stimulation electrodes may be disposed on the circumference of the lead to stimulate the target neurons. Stimulation electrodes may be ring-shaped so that current projects from each electrode equally in every direction at any given length along the axis of the lead. To achieve current steering, segmented electrodes can be utilized additionally or alternatively. Though the following description discusses stimulation electrodes, it will be understood that all configurations of the stimulation electrodes discussed may be utilized in arranging recording electrodes as well.

Figure 1A:
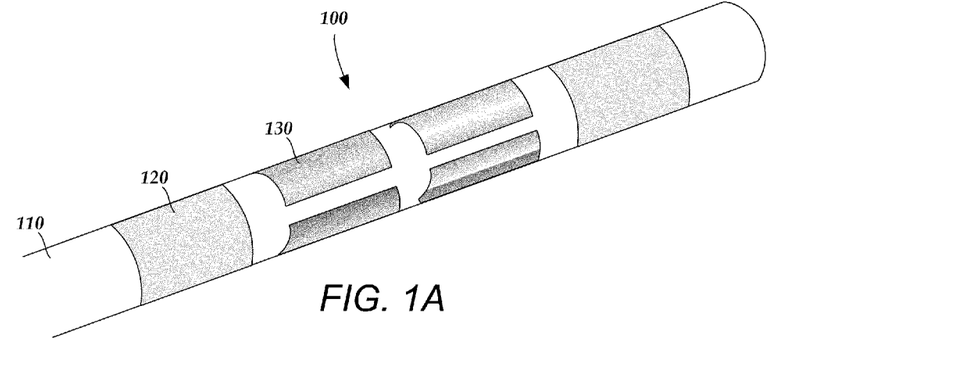
FIG. 1A is a schematic perspective view of one embodiment of a portion of a lead having a plurality of segmented electrodes, according to the invention.

FIG. 1A illustrates one embodiment of a lead 100 for brain stimulation. The device includes a lead body 110, one or more ring electrodes 120, and a plurality of segmented electrodes 130. The lead body 110 can be formed of a biocompatible, non-conducting material such as, for example, a polymeric material. Suitable polymeric materials include, but are not limited to, silicone, polyurethanes, polyethylene, or polyureas. In at least some instances, the lead may be in contact with body tissue for extended periods of time. In at least some embodiments, the lead has a cross-sectional diameter of no more than 1.5 mm and may be in the range of 0.75 to 1.5 mm. In at least some embodiments, the lead has a length of at least 10 cm and the length of the lead may be in the range of 25 to 70 cm.

Stimulation electrodes may be disposed on the lead body 110. These stimulation electrodes may be made using a metal, alloy, conductive oxide, or any other suitable conductive material. Examples of suitable materials include, but are not limited to, platinum, platinum iridium alloy, iridium, stainless steel, titanium, or tungsten. Preferably, the stimulation electrodes are made of a material that is biocompatible and does not substantially corrode under expected operating conditions in the operating environment for the expected duration of use.

In at least some embodiments, any of the electrodes can be used as an anode or cathode and carry anodic or cathodic current. In some instances, an electrode might be an anode for a period of time and a cathode for a period of time. In other embodiments, the identity of a particular electrode or electrodes as an anode or cathode might be fixed.

Stimulation electrodes in the form of ring electrodes 120 may be disposed on any part of the lead body 110, usually near a distal end of the lead. FIG. 1A illustrates a portion of a lead having two ring electrodes. Any number of ring electrodes, or even a single ring electrode, may be disposed along the length of the lead body 110. For example, the lead body may have one ring electrode, two ring electrodes, three ring electrodes or four ring electrodes. In some embodiments, the lead will have five, six, seven or eight ring electrodes.

In some embodiments, the ring electrodes 120 are substantially cylindrical and wrap around the entire circumference of the lead body 110. In some embodiments, the outer diameter of the ring electrodes 120 is substantially equal to the outer diameter of the lead body 110. Furthermore, the width of ring electrodes 120 may vary according to the desired treatment and the location of the target neurons. In some embodiments the width of the ring electrode 120 is less than or equal to the diameter of the ring electrode 120. In other embodiments, the width of the ring electrode 120 is greater than the diameter of the ring electrode 120.

In at least some embodiments, the lead also contains a plurality of segmented electrodes 130. Any number of segmented electrodes 130 may be disposed on the lead body 110. In some embodiments, the segmented electrodes 130 are grouped in sets of segmented electrodes, each set disposed around the circumference of the lead at or near a particular longitudinal position. The lead may have any number of sets of segmented electrodes. In at least some embodiments, the lead has one, two, three, four, five, six, seven, or eight sets of segmented electrodes. In at least some embodiments, each set of segmented electrodes contains the same number of segmented electrodes 130. In some embodiments, each set of segmented electrodes contains three segmented electrodes 130. In at least some other embodiments, each set of segmented electrodes contains two, four, five, six, seven or eight segmented electrodes. The segmented electrodes 130 may vary in size and shape. In some embodiments, the segmented electrodes 130 are all of the same size, shape, diameter, width or area or any combination thereof. In some embodiments, the segmented electrodes of each set (or even all segmented electrodes) may be identical in size and shape.

In at least some embodiments, each set of segmented electrodes 130 may be disposed around the circumference of the lead body 110 to form a substantially or approximately cylindrical shape around the lead body 110. The spacing of the segmented electrodes 130 around the circumference of the lead body 110 may vary. In at least some embodiments, equal spaces, gaps or cutouts are disposed between each segmented electrodes 130 around the circumference of the lead body 110. In other embodiments, the spaces, gaps or cutouts between segmented electrodes may differ in size or shape. In other embodiments, the spaces, gaps, or cutouts between segmented electrodes may be uniform for a particular set of segmented electrodes or for all sets of segmented electrodes. The segmented electrodes 130 may be positioned in irregular or regular intervals around the lead body 110.

Conductors (not shown) that attach to or from the ring electrodes 120 and segmented electrodes 130 also pass through the lead body 110. These conductors may pass through the material of the lead or through a lumen defined by the lead. The conductors are presented at a connector for coupling of the electrodes to a control unit (not shown). In one embodiment, the stimulation electrodes correspond to wire conductors that extend out of the lead body 110 and are then trimmed or ground down flush with the lead surface (after they are connected to an electrode). The conductors may be coupled to a control unit to provide stimulation signals, often in the form of pulses, to the stimulation electrodes.

Figure 1B:
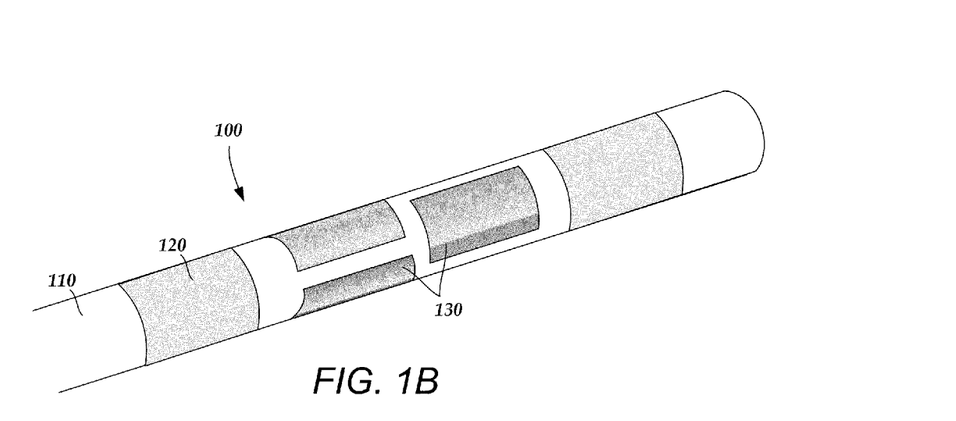
FIG. 1B is a schematic perspective view of another embodiment of a portion of a lead having a plurality of segmented electrodes arranged in a staggered orientation, according to the invention.

FIG. 1B is a schematic side view of another embodiment of a lead having a plurality of segmented electrodes. As seen in FIG. 1B, the plurality of segmented electrodes 130 may be arranged in different orientations relative to each other. In contrast to FIG. 1A, where the two sets of segmented electrodes are aligned along the length of the lead body 110, FIG. 1B displays another embodiment in which the two sets of segmented electrodes 130 are staggered. In at least some embodiments, the sets of segmented electrodes are staggered such that no segmented electrodes are aligned along the length of the lead body 110. In some embodiments, the segmented electrodes may be staggered so that at least one of the segmented electrodes is aligned with another segmented electrode of a different set, and the other segmented electrodes are not aligned.

Any number of segmented electrodes 130 may be disposed on the lead body 110 in any number of sets. FIGS. 1A and 1B illustrate embodiments including two sets of segmented electrodes. These two sets of segmented electrodes 130 may be disposed in different configurations. For example, two sets of segmented electrodes 130 may be disposed on the distal end of the lead body 110, distal to the two ring electrodes 120. Alternatively, two sets of segmented electrodes 130 may be disposed proximal to the two ring electrodes 120. By varying the location of the segmented electrodes 130, different coverage of the target neurons may be selected. For example, a specific configuration may be useful if the physician anticipates that the neural target will be closer to the distal tip of the lead body 110, while another arrangement may be useful if the physician anticipates that the neural target will be closer to the proximal end of the lead body 110. In at least some embodiments, the ring electrodes 120 alternate with sets of segmented electrodes 130.

Any combination of ring electrodes 120 and segmented electrodes 130 may be disposed on the lead. In some embodiments the segmented electrodes are arranged in sets. For example, a lead may include a first ring electrode 120, two sets of segmented electrodes, each set formed of three segmented electrodes 130, and a final ring electrode 120 at the end of the lead. This configuration may simply be referred to as a 1-3-3-1 configuration. It may be useful to refer to the electrodes with this shorthand notation. Other eight electrode configurations include, for example, a 2-2-2-2 configuration, where four sets of segmented electrodes are disposed on the lead, and a 4-4 configuration, where two sets of segmented electrodes, each having four segmented electrodes 130 are disposed on the lead. In some embodiments, the lead will have 16 electrodes. Possible configurations for a 16-electrode lead include, but are not limited to 4-4-4-4, 8-8, 3-3-3-3-3-1 (and all rearrangements of this configuration), and 2-2-2-2-2-2-2-2.

Figure 2:
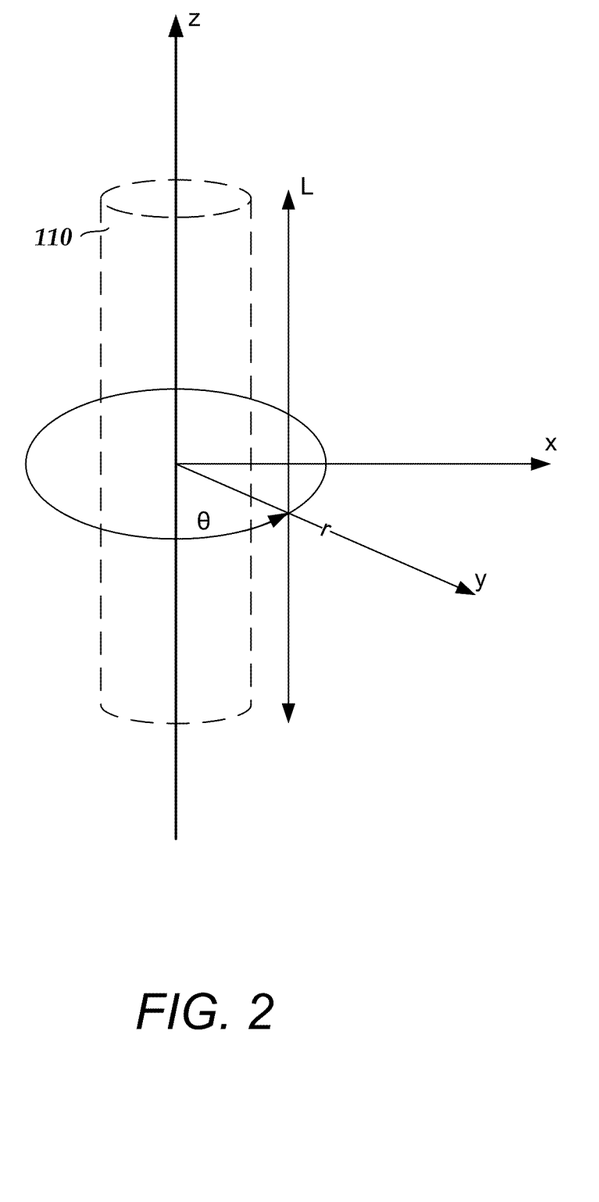
FIG. 2 is a schematic diagram of radial current steering along various electrode levels along the length of a lead, according to the invention.

FIG. 2 is a schematic diagram to illustrate radial current steering along various electrode levels along the length of a lead. While conventional lead configurations with ring electrodes are only able to steer current along the length of the lead (the z-axis), the segmented electrode configuration is capable of steering current in the x-axis, y-axis as well as the z-axis. Thus, the centroid of stimulation may be steered in any direction in the three-dimensional space surrounding the lead body 110. In some embodiments, the radial distance, r, and the angle θ around the circumference of the lead body 110 may be dictated by the percentage of anodic current (recognizing that stimulation predominantly occurs near the cathode, although strong anodes may cause stimulation as well) introduced to each electrode as will be described in greater detail below. In at least some embodiments, the configuration of anodes and cathodes along the segmented electrodes 130 allows the centroid of stimulation to be shifted to a variety of different locations along the lead body 110.

As can be appreciated from FIG. 2, the centroid of stimulation can be shifted at each level along the length of the lead. The use of multiple sets of segmented electrodes 130 at different levels along the length of the lead allows for three-dimensional current steering. In some embodiments, the sets of segmented electrodes 130 are shifted collectively (i.e. the centroid of simulation is similar at each level along the length of the lead). In at least some other embodiments, each set of segmented electrodes 130 is controlled independently. Each set of segmented electrodes may contain two, three, four, five, six, seven, eight or more segmented electrodes. It will be understood that different stimulation profiles may be produced by varying the number of segmented electrodes at each level. For example, when each set of segmented electrodes includes only two segmented electrodes, uniformly distributed gaps (inability to stimulate selectively) may be formed in the stimulation profile. In some embodiments, at least three segmented electrodes 130 are utilized to allow for true 360° selectivity.

As previously indicated, the foregoing configurations may also be used while utilizing recording electrodes. In some embodiments, measurement devices coupled to the muscles or other tissues stimulated by the target neurons or a unit responsive to the patient or clinician can be coupled to the control unit or microdrive motor system. The measurement device, user, or clinician can indicate a response by the target muscles or other tissues to the stimulation or recording electrodes to further identify the target neurons and facilitate positioning of the stimulation electrodes. For example, if the target neurons are directed to a muscle experiencing tremors, a measurement device can be used to observe the muscle and indicate changes in tremor frequency or amplitude in response to stimulation of neurons. Alternatively, the patient or clinician may observe the muscle and provide feedback.

Regardless of the type of electrodes used, proper placement of the lead may be important in providing proper and adequate treatment. For example, in some cases, a target may be located on one side of a plane running through the axis of the lead. In other cases, a target may be located at a plane that is offset at some angle from the axis of the lead. Thus, it is desirable to be able to radially adjust the location of the lead such that the appropriate vertical level of electrodes is in a desired radial alignment with the target tissue. Various systems and methods may be used for radial steering of a radially segmented electrode.

First, systems and methods are needed to measure or determine the position of the lead within the brain. Radial steering of stimulation benefits from the ability to accurately determine the relative position of the electrodes. Systems and methods are desirable to position and rotate the lead accordingly in order to establish alignment and provide therapy.

Figure 3A:
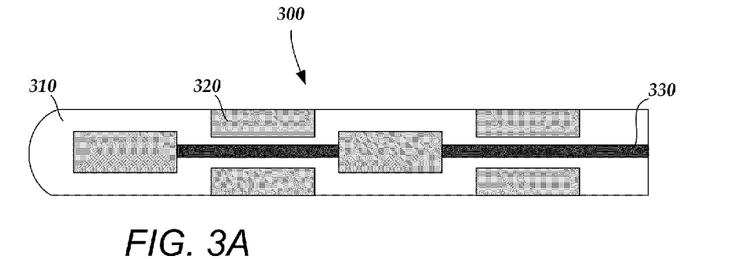
FIG. 3A is a schematic side view of one embodiment of a lead having a marking stripe in alignment with a set of electrodes, according to the invention.
Figure 3B:
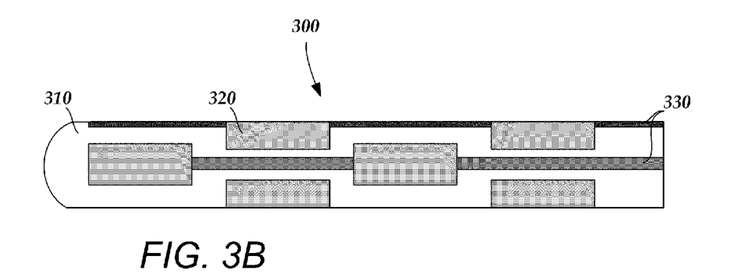
FIG. 3B is a schematic side view of another embodiment of a lead having two marking stripes in alignment with a set of electrodes, according to the invention.
Figure 3C:
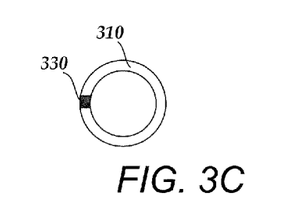
FIG. 3C is a schematic cross-sectional view of the lead having a marking stripe of FIG. 3A, according to the invention.

In some embodiments, a device for brain stimulation comprises a lead having a longitudinal surface, a proximal end and a distal end. A plurality of electrodes are disposed along the longitudinal surface of the lead near the distal end of the lead and a marker is disposed on the longitudinal surface of the lead. The marker may be configured to identify the relative position of the plurality of electrodes. A user, observing the position of the marker, can determine the orientation of the lead and the positions of the electrodes relative to the surroundings (e.g., the tissue of the brain). Observation of the marker can be by one or more techniques including, but not limited to, visual observation, radiographic observation, spectroscopic observation and the like. FIG. 3A illustrates one embodiment of a lead 300 having a lead body 310, a plurality of electrodes 320 and a marker in the form of a marking stripe 330. FIG. 3C is a schematic cross-sectional view of the lead 300 of FIG. 3A. The marking stripe 330 may be any of a band, ribbon, streak, strip or a longitudinal striation disposed along a portion of the length of the lead. In some embodiments, the marking stripe 330 is disposed parallel to the central axis of the lead body 310.

In some embodiments, the marking stripe 330 is coextruded with the lead body 310. In some other embodiments, the marking stripe 330 is applied to or within an outer layer of insulation of a lead body 310 after the lead body 310 has been formed. The marking stripe 330 may be applied using an indelible ink. Alternatively, the marking stripe 330 may also be formed by ablating the outer layer of the lead body 310 using, for example, laser ablation. FIGS. 3A and 3C illustrate a marking stripe 330 that is disposed on the most outer layer insulation of the lead body 310. Alternatively, the marking stripe 330 may be disposed on the inside or closer to the center of the lead body 310.

In some embodiments, the marking stripe 330 is radioopaque. A radioopaque marking stripe 330 may allow for visualization of the relative position of the plurality of electrodes 320 through visual inspection or radiological methods. Thus, any portion of the marking stripe 330 or the entire marking stripe 330 may be radioopaque. In some embodiments, the radioopaque material includes barium sulfate. In some embodiments, the radioopaque material includes titanium dioxide. Alternatively, the marking stripe may be a metallic element that is disposed into the lead body. Materials for the metallic element include, for example, biocompatible materials, such as stainless steel, titanium, platinum, platinum iridium, and the like.

Figure 3D:
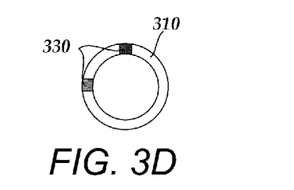
FIG. 3D is a schematic cross-sectional view of the lead having two marking stripes of FIG. 3B, according to the invention.

Different configurations and arrangements of the marking stripe 330 are possible. For example, FIGS. 3A and 3C illustrate a lead 300 having a single marking stripe 330. Conversely, a plurality of marking stripes may be disposed on the lead 300. For example, in another embodiment, shown in FIG. 3B, the lead 300 has two marking stripes 330. FIG. 3D illustrates a cross-sectional view of the lead 300 of FIG. 3B. It will be understood that any number of marking stripes 330 may be disposed on the lead 300. For example, one, two, three, four, five, six, seven, eight, nine or ten marking stripes 330 may be disposed on the lead. Furthermore, the lead stripes 330 may be disposed in a variety of arrangements. As seen in FIGS. 3B and 3D, the marking stripes 330 may be disposed 90 degrees apart on the lead 300. In some embodiments, the marking stripes are disposed 10, 20, 30, 45, 60, 80 or 120 degrees apart. It will be understood that multiple marking stripes can be separated by any angle as desired. In some embodiments, the marking stripes are disposed at an angle other than 180 degrees to determine the forward/backward position through radiographic methods. When the marking stripes are at a position of 180 degrees, it may be possible to determine the position of the lead, without determining the forward/backward placement of the lead. Thus, in some embodiments, the two marking stripes are not antipodal, i.e. that they are not disposed on diametrically opposite sides of the cross-section of the lead body 310. Positioning of the lead will be further explained with reference to FIGS. 4A-F.

In some embodiments, the marking stripes 330 may be of different colors. For example, one or more marking stripes 330 may be a first color, while one or more marking stripes 330 on the opposite side of the lead 300 may be a second color. In some embodiments, each marking stripe 330 is a distinct color. The marking stripes may also be different shades of the same color. For example, a first marking stripe may be a particular color, while second and third marking stripes are progressively darker shades of the same color. Alternatively, the marking stripes 330 may be of different widths. In some embodiments, the lumens stripes may begin with a single thin marking stripe 330, with successive lumens stripes 330 progressively increasing in width around the perimeter of the lead. Any combination of thin and wide marking stripes is possible. Additionally, the marking stripes 330 may also be of different textures or configurations. Any configuration of the marking stripes 330 may be utilized, so long as they are able to denote a given electrode level and a radial position. Alternatively, the marking stripes may have different radiographic properties; for example, some stripes may appear darker than others when imaged.

Figure 4A:
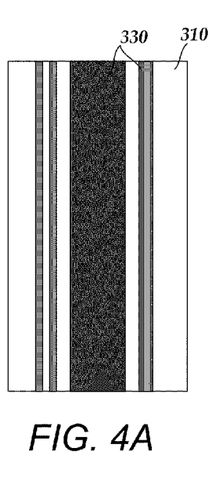
FIG. 4A is a schematic radiographic image through the side of a lead having multiple marking stripes 330 disposed in a first position, according to the invention.
Figure 4B:
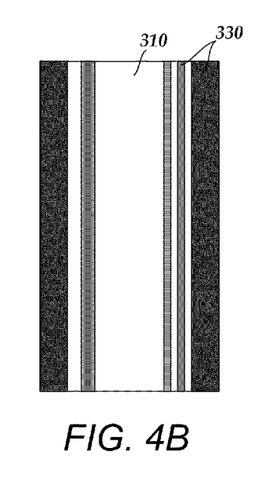
FIG. 4B is a schematic radiographic image of the lead of FIG. 4A disposed in a second position, according to the invention.
Figure 4C:
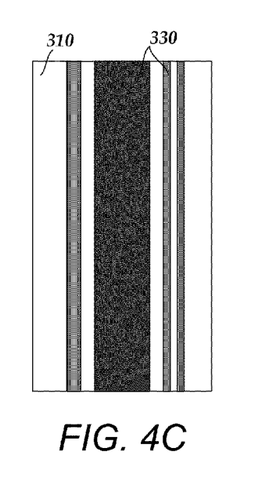
FIG. 4C is a schematic radiographic image of the lead of FIG. 4A disposed in a third position, according to the invention.
Figure 4D:
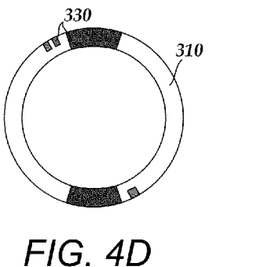
FIG. 4D is a schematic cross-sectional view of the lead of FIG. 4A in the first position, according to the invention.
Figure 4E:
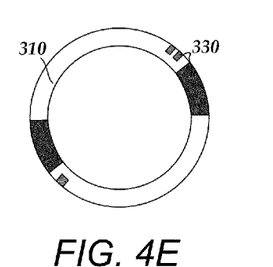
FIG. 4E is a schematic cross-sectional view of the lead of FIG. 4B in the second position, according to the invention.
Figure 4F:
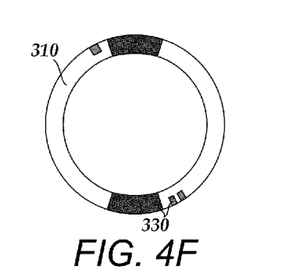
FIG. 4F is a schematic cross-sectional view of the lead of FIG. 4C in the third position, according to the invention.

FIG. 4A is a schematic radiographic image through the side of a lead having multiple marking stripes 330 disposed in a first position. FIG. 4B is a schematic radiographic image of the lead of FIG. 4A disposed in a second position. FIG. 4C is a schematic radiographic image of the lead of FIG. 4A disposed in a third position. The corresponding cross-sectional view of the leads of FIGS. 4A-C are illustrated in FIGS. 4D-F. Thus, one of ordinary skill in the art seeing a radiographic image similar to FIG. 4A will understand that the lead is radially positioned in the orientation of FIG. 4D. Similarly, one of ordinary skill in the art seeing a radiographic image similar to FIG. 4B will understand that the lead is radially positioned in the orientation of FIG. 4E and so on. Thus, the radial position of the lead, with respect to the anatomy, may be determined by examining the marking stripes disposed on the lead.

Figure 5:
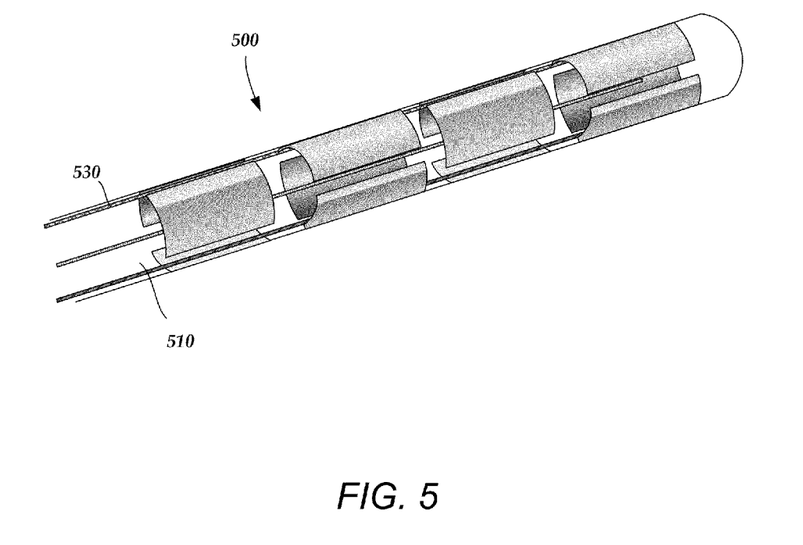
FIG. 5 is a schematic perspective view of one embodiment of a lead illustrating colored cables attached to each of the distal electrodes, according to the invention.

In some embodiments, a colored cable 510 may be utilized instead of the marking stripe described above, or in addition to the marking stripe. FIG. 5 is a perspective view of another embodiment of a lead where the marker is in the form of a colored cable 510. FIG. 5 illustrates a portion of a lead 500 having a lead body 510 and a colored cable 530. For ease of illustration, only the colored cables attached to the distal-most electrodes are shown. The colored cable 530 is a cable with an insulation material that contains a colorant. In some embodiments, the colored cable 530 includes an insulative polymeric material including, but not limited to ethylene tetrafluoroethylene, polyfluoroalkoxy polymers, polytetrafluoroethylene, silicone, polyurethane, and polyethylene. Any biocompatible colorant may be used to color the insulation of the cable. In some embodiments, different colorants are used to differentiate the cables.

The colored cables may be of different sizes. For example, in some embodiments, multiple colored cables 530 are formed to have different diameters. Because the colored cables may also be radioopaque, having colored cables 530 of different diameters may be useful in determining the position and orientation of the lead using radiographic methods. In at least some other embodiments, the colored cables are of different lengths. For example, a colored cable 530 may extend the entire length of the lead body 510 or only through a portion of the lead body 510.

In some embodiments, the colored cable 530 may be located within a lumen of the lead body 510 so as to be integrated into the lead body 510. The lumen housing the colored cable may extend longitudinally throughout the entire length of, or through a portion of, the lead body 510. The lumen housing the colored cable may run parallel to the central axis of the lead body 510. In at least some embodiments, multiple lumens may be disposed on the periphery of the lead body 510 to house a plurality of colored cables 530.

In embodiments having multiple lumens to house a plurality of colored cables 530, each lumen and colored cable may be configured and arranged as described above. Thus, any combination of multiple colored cables 530, such as for example, colored cable 530 having different colors or different diameters may be integrated within the lead body 510.

In addition to markers disposed on the lead body, additional components may be useful in positioning and rotating the lead. In some embodiments, an aligning member is used to adjust the location of the lead. The aligning member may have a marking that corresponds to the marker on the lead. For example, in some embodiments, the aligning member has a marking at a position that corresponds to the position of the marking stripe on the lead. In some other embodiments, the aligning member has a marking at a position that corresponds to the position of a colored cable. It will be understood that the term "correspond" implies that any position of the marking on the aligning member may be used so long as the marking indicates the position of the lead relative to the aligning member. In other words, a marking may be disposed on the aligning member such that a physician using the aligning member is capable of appreciating the position of the lead during a procedure. In some embodiments, the aligning member serves as both a marker and a tool for adjustment.

The use of an aligning member may include a variety of elements and procedures as will be described below. It will be understood that any combination of the aligning members discussed below may be used. Additionally, the aligning members may be used in conjunction with any marker on the lead, such as a marking stripe, a colored cable, or a combination of the two.

In some embodiments, the aligning member is a cannula. The cannula may be coupled to the lead and used to radially steer the lead to the proper orientation. The cannula can be formed of any suitable material such as, for example, a plastic material. Preferably, the cannula is formed of a substantially rigid material which facilitates insertion of the cannula into the brain of the patient and positioning of the cannula and electrode lead near the tissue to be stimulated. In some embodiments, the cannula is a disposable unit so that it is discarded after use and does not need to be subsequently sterilized for reuse.

The cannula may be mechanically coupled to the lead to act as a steering mechanism. In some embodiments, the cannula may be coupled to the lead such that there is no relative movement between the cannula and the lead. Coupling the cannula to the lead may be accomplished using a variety of methods. In some embodiments, the cannula has a handle, having a locking mechanism, such as a set screw, collet, or the like that is secured to the lead body. As previously indicated, the cannula may include a marker corresponding to a marker on the lead.

Figure 6A:
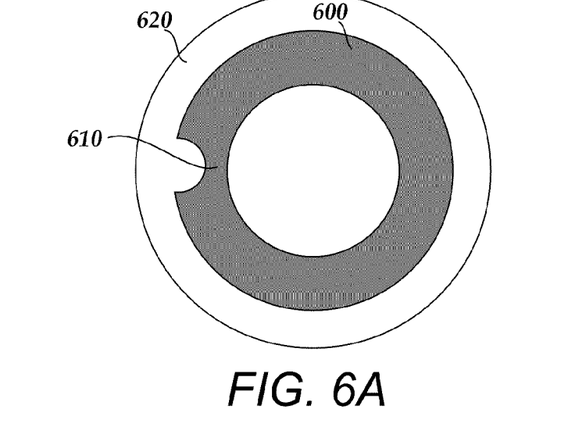
FIG. 6A is a schematic cross-sectional view of one embodiment of a lead having a keyed portion, according to the invention.
Figure 6B:
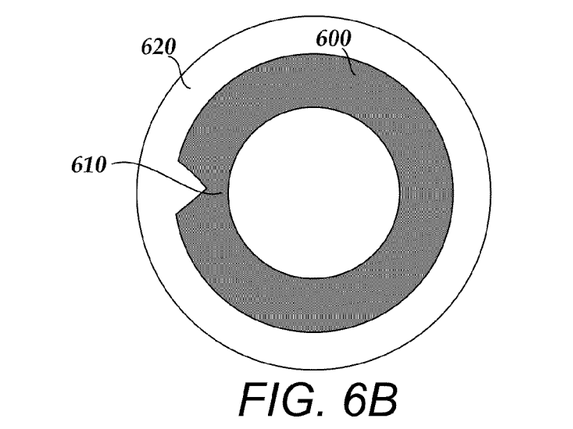
FIG. 6B is a schematic cross-sectional view of a second embodiment of a lead having a keyed portion, according to the invention.
Figure 6C:
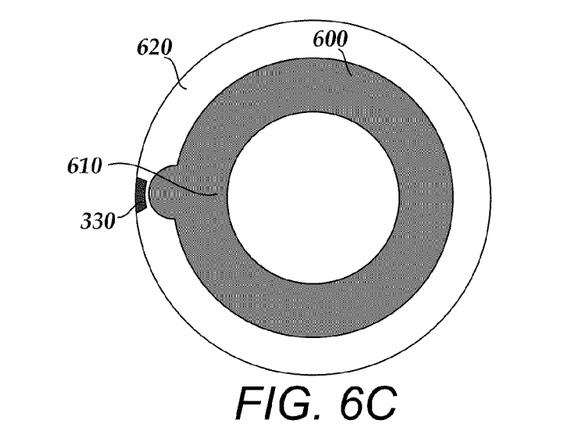
FIG. 6C is a schematic cross-sectional view of a third embodiment of a lead having a keyed portion, according to the invention.

In at least some embodiments, the cannula is configured to mate with the lead. FIG. 6A is a schematic cross-sectional view of one embodiment of a lead 600 having a keyed portion 610 of the lead body. As seen in FIG. 6A, in some embodiments, the lead body is modified to add a keyed or trimmed portion. In some embodiments, the keyed portion 610 is configured to mate with a corresponding external component such as the cannula 620 described above. FIG. 6A also illustrates a cannula 620 corresponding to the keyed portion 610 of the lead 600. It will be understood that the keyed portion 610 may be configured to also mate with a stereotactic frame adapter or a stylet to provide radial steering as will be described in more detail below. It will also be understood that the keyed portion 610 may itself act as a marker by being disposed at a given electrode level or radial position. FIG. 6B is a schematic cross-sectional view of another embodiment of a lead having a keyed portion 610 in the form of a triangle. As seen in FIG. 6B, the keyed portion 610 may be of a different shape than the generally circular shape of FIG. 6A. Any shape may be used for the keyed portion 610. Additionally, regardless of the shape of the keyed portion 610, the cannula 620 may also have a shape that corresponds to it. FIG. 6C illustrates another embodiment in which the keyed portion 610 extends into the cannula 620.

In some embodiments, only the proximal end of the lead includes a keyed feature. The keyed proximal end may be used instead of or in addition to the keyed portion discussed above. In some embodiments, the keyed proximal end includes a keyed or grooved portion that engages with an aligning member such as a cannula. Additionally, it will be understood that the keyed feature of the proximal end may correspond to a given electrode level and radial position. Thus, it is possible to include a marker such as a colored cable or a marking stripe in addition to the keyed proximal end, and it may also be possible to determine the orientation of the lead using the keyed proximal end alone. In some embodiments, the keyed proximal end is disposed on a position of the lead body so that it corresponds to a marker or marking stripe on the aligning member.

As previously discussed, the keyed proximal end may be used in conjunction with a cannula. In these embodiments, the keyed proximal end is configured to engage or mate with the cannula so that radial steering is possible. In some other embodiments, the keyed proximal end is configured to couple with an aligning member other than a cannula, such as for example a stereotactic frame adaptor or a stylet.

Figure 7:
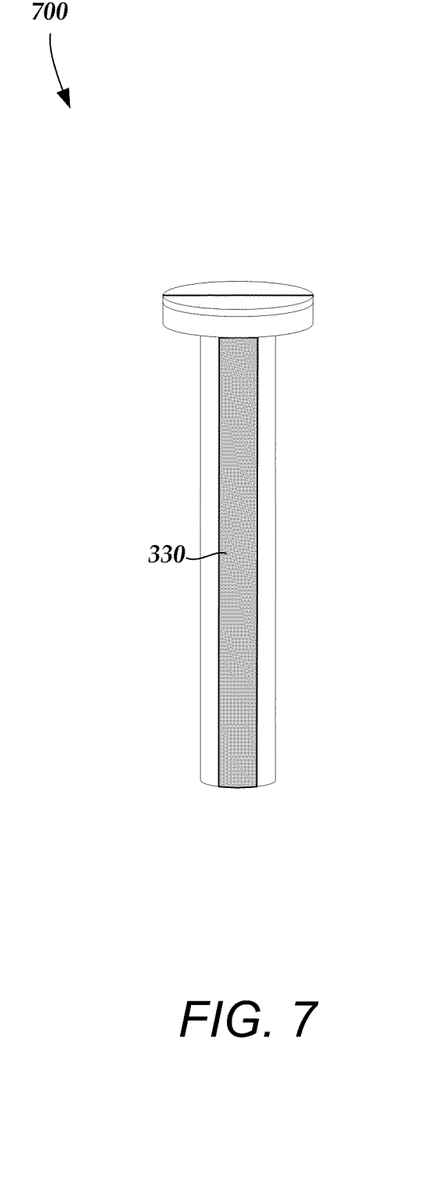
FIG. 7 is a schematic perspective view of one embodiment of a stereotactic frame insert having a marker stripe, according to the invention.

FIG. 7 is a schematic perspective view of one embodiment of a stereotactic frame insert. Due to the delicate nature of the brain, the stereotactic frame may be used to stabilize the area of operation so that therapy may be applied to a predefined area. A stereotactic frame may include a stereotactic frame insert used to position the lead within the cranium of the patient. In some embodiments, a stereotactic frame insert 700 is temporarily affixed to the patient's head for treatment.

The stereotactic frame may include a stereotactic frame insert 700 such as that seen in FIG. 7. In some embodiments, the stereotactic frame insert 700 is configured to allow for mating with a lead. The lead and stereotactic frame insert 700 may be coupled through any method known in the art, or through the use of a keyed portion or a keyed proximal portion as described above. In some embodiments, the stereotactic frame insert 700 includes a marker that will correspond to a given electrode level or to a marker disposed on the lead. For example the stereotactic frame insert may be made to include a feature that matches a feature on the lead, such as one of those described in the above embodiments (e.g. a marking stripe, a colored cable, or a keyed portion).

A stereotactic frame adaptor may also be useful in providing proper alignment and connection to a lead. The stereotactic frame adapter may contain a marker, such as marking stripe 330, as discussed above with respect to the stereotactic frame insert. The stereotactic frame adaptor may be modified to provide alignment and connection to the lead, in addition to alignment and relative movement to the stereotactic frame. Thus, to radially steer the lead, the stereotactic frame insert may be rotated within the stereotactic frame.

In addition to or as an alternative to a cannula and a stereotactic frame, the aligning member may include a stylet. In some embodiments, a lead for deep brain stimulation defines a lumen within the lead for the insertion of a removable stylet. As seen in FIG. 10, the use of a stylet can facilitate insertion of the lead into the cranium and brain tissue, thus facilitating positioning of the lead to stimulate the target neurons. Furthermore, the stylet can provide rigidity to the lead during the insertion process.

Figure 8A:
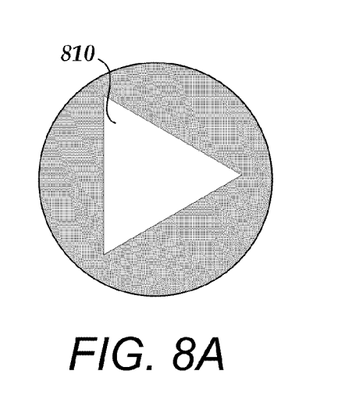
FIG. 8A is a schematic perspective view of one embodiment of a stylet lumen, according to the invention.
Figure 8B:
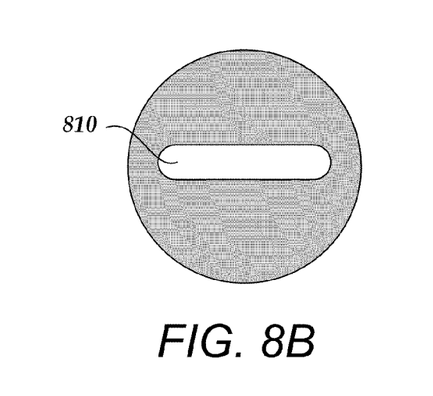
FIG. 8B is a schematic perspective view of a second embodiment of a stylet lumen, according to the invention.
Figure 8C:
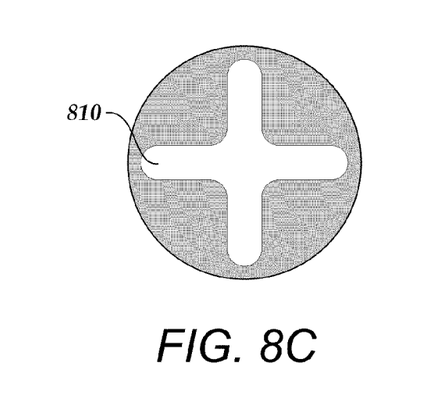
FIG. 8C is a schematic perspective view of a third embodiment of a stylet lumen, according to the invention.

FIGS. 8A-C illustrate several embodiments of a lumen configured for the insertion of a stylet. As seen in these figures, the lumen 810 can have any shape. For example, FIG. 8A illustrates a lead having a lumen 810 in the shape of a triangle. Alternatively, the lumen 810 may be in the shape of a rectangle with rounded edges as illustrated in FIG. 8B, or a lumen 810 in the shape of a cruciform as illustrated in FIG. 8C. In some embodiments, the lateral cross-sectional shape of the lumen 810 is non-circular. For example, the lateral cross-sectional shape of the lumen 80 may be an oval, square, rectangular, or a cruciform shape.

The stylet may also have a corresponding lateral cross-sectional shape. For example, a stylet may have a cruciform shape corresponding to the shape of the lumen as illustrated in FIG. 8C. The non-circular lateral cross-sectional shape can permit the practitioner to rotate the lead by rotating the stylet. A non-circular stylet lumen and stylet may be used to provide for better one-to-one torque transmission of the lead/stylet assembly. Because the lumen is non-circular, the stylet can not rotate within the lead and, therefore, rotation of the stylet results in rotation of the lead. A cruciform shaped lumen can be particularly useful, as opposed to an oval, square or rectangular lumen, if the shape of the lumen might be deformed by rotation of the stylet because the lead is not sufficiently rigid. Shapes similar to cruciform, with multiple arms extending from a central cavity, such as an asterisk- or star-shaped lumen and corresponding stylet, can be similarly useful.

In some embodiments, the stylet is made of a rigid material such as, for example, tungsten or a plastic. The stylet may also have a handle to assist insertion into the lead, as well as rotation of the stylet and lead. As discussed with reference to the cannula and the stereotactic frame, it will be understood that the stylet handle may include a marker that corresponds to a marker on the lead.

Figure 9:
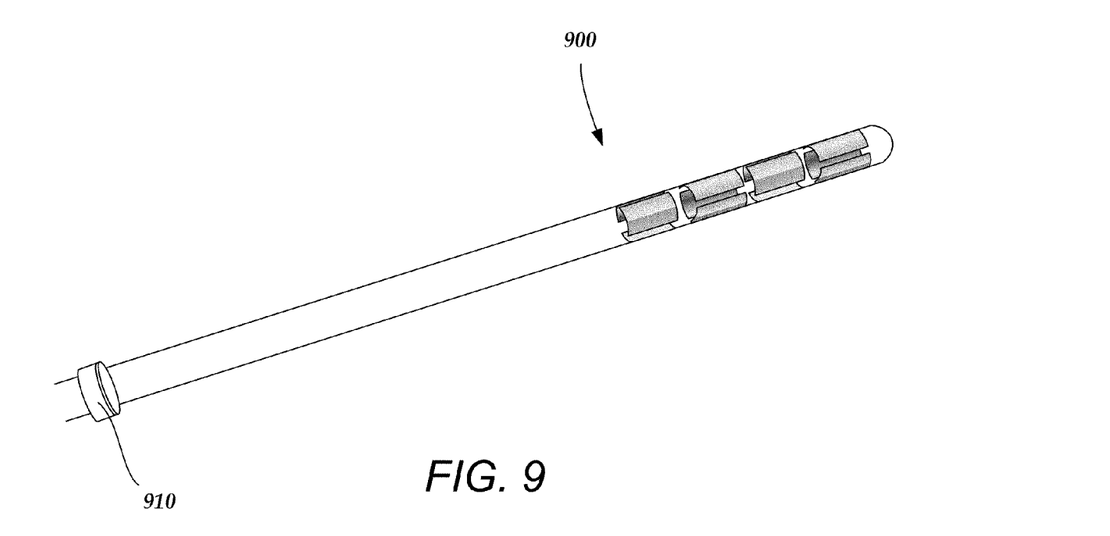
FIG. 9 is a schematic perspective view of one embodiment of a lead having a lead stop, according to the invention.

A lead stop may also be used to rotate and align the lead. FIG. 9 is a schematic perspective view of one embodiment of a lead 900 having a lead stop 910. The lead stop 910 may be engaged with the outer diameter of the lead 900. In some embodiments, the lead stop 910 is disposed on the proximal end of the lead 900 and configured to position the lead 900 at a predetermined longitudinal position. The lead stop 910 may be used in combination with a lead stripe or a colored cable to indicate a given electrode level and radial position. In some embodiments, the lead stop 910 may also include a marking that corresponds to an electrode level or a marker disposed on the lead 900.

Modifications of these methods are possible. For example, two or more of these methods may be used in combination to provide a more accurate radial steering mechanism. Furthermore, in some embodiments, these methods are used with lead constructions other than deep brain stimulation leads.

The above specification, examples and data provide a description of the manufacture and use of the composition of the invention. Since many embodiments of the invention can be made without departing from the spirit and scope of the invention, the invention also resides in the claims hereinafter appended.

What is claimed as new and desired to be protected by Letters Patent of the United States is:

1. A device for electrical stimulation, comprising:
a lead having a longitudinal surface, a circumference, a proximal end and a distal end;
a plurality of segmented electrodes disposed along the longitudinal surface of the lead near the distal end of the lead, wherein the plurality of segmented electrodes comprises at least one set of segmented electrodes, each set having two or more of the segmented electrodes disposed around the circumference of the lead at a particular longitudinal position; and
at least two longitudinal marking stripes disposed on the longitudinal surface of the lead and with a portion of each of the marking stripes disposed between two of the segmented electrodes of one of the at least one set of segmented electrodes, the at least two marking stripes being configured and arranged to identify a relative position of the plurality of segmented electrodes.

2. The device of claim 1, wherein the at least two of the at least two marking stripes are not antipodal.

3. The device of claim 1, wherein the at least two marking stripes are different in at least one of color, width, or texture.

4. The device of claim 1, wherein the at least two marking stripes are different in color.

5. The device of claim 1, wherein the at least two marking stripes comprise a radioopaque material.

6. The device of claim 1, further, comprising:
a first keyed feature extending longitudinally along the proximal end of the lead; and
an aligning member insertable into a lumen of the lead, the aligning member comprising a second keyed feature that engages the first keyed feature along the proximal end of the lead, wherein the aligning member has a non-circular cross-section corresponding to a non-circular cross-section of the lumen.

7. The device of claim 6, wherein the aligning member comprises a stereotactic frame insert that is insertable into the lumen of the lead.

8. The device of claim 6, wherein the aligning member comprises a stylet insertable into the lumen of the lead.

9. The device of claim 6, wherein the aligning member comprises a lead stop.

10. A method for brain stimulation, the method comprising:
inserting the device of claim 6 into a cranium of a patient; and
aligning the lead to a selected position using the aligning member.

11. The method of claim 10, wherein the aligning member is a stylet.

12. The method of claim 11, further comprising rotating the lead using the stylet.

13. An implantable stimulation device, comprising:
the device of claim 1, and
a control unit coupleable to the lead.

14. The implantable stimulation device of claim 13, wherein the implantable stimulation device is a deep brain stimulator.

15. A method for brain stimulation, the method comprising:
inserting the device of claim 1 into a cranium of a patient; and
aligning the lead to a selected position using the at least two marking stripes.

16. The device of claim 1, wherein the at least two marking stripes are different in width.

17. The device of claim 1, wherein the at least two marking stripes comprise a first marking stripe, a second marking stripe extending parallel to and adjacent the first marking stripe, and a third marking strip extending parallel to and disposed circumferentially opposite the first marking stripe.

18. The device of claim 17, wherein the third marking stripe is wider than the first marking stripe and the second marking stripe individually.

19. The device of claim 1, wherein the at least one set of segmented electrodes comprises a first set of segmented electrodes and a second set of segmented electrodes which is at a different longitudinal position from the first set.

20. The device of claim 1, wherein at least one of the at least two marking stripes extends between one of the segmented electrodes of the first set and one of the segmented electrodes of the second set.

\* \* \* \* \*